United States Patent
Chan et al.

(10) Patent No.: US 11,723,359 B2
(45) Date of Patent: Aug. 15, 2023

(54) DISPOSABLE ANTIMICROBIAL WIPES AND METHODS OF MAKING

(71) Applicant: Ecolab USA Inc., St. Paul, MN (US)

(72) Inventors: Wendy Chan, St. Paul, MN (US); Sherri Tischler, Inver Grove Heights, MN (US)

(73) Assignee: ECOLAB USA INC., St. Paul, MN (US)

( * ) Notice: Subject to any disclaimer, the term of this patent is extended or adjusted under 35 U.S.C. 154(b) by 23 days.

(21) Appl. No.: 16/830,737

(22) Filed: Mar. 26, 2020

(65) Prior Publication Data

US 2020/0288708 A1 Sep. 17, 2020

Related U.S. Application Data

(63) Continuation of application No. 14/682,663, filed on Apr. 9, 2015, now abandoned.

(51) Int. Cl.

| | |
|---|---|
| *A01N 25/34* | (2006.01) |
| *A01N 33/12* | (2006.01) |
| *A61K 8/365* | (2006.01) |
| *A61Q 17/00* | (2006.01) |
| *D04H 1/4258* | (2012.01) |
| *A47L 13/17* | (2006.01) |
| *A01N 25/10* | (2006.01) |
| *A61K 8/41* | (2006.01) |
| *A61K 8/02* | (2006.01) |
| *A61K 8/36* | (2006.01) |

(52) U.S. Cl.
CPC ............ *A01N 25/34* (2013.01); *A01N 25/10* (2013.01); *A01N 33/12* (2013.01); *A47L 13/17* (2013.01); *A61K 8/0208* (2013.01); *A61K 8/36* (2013.01); *A61K 8/365* (2013.01); *A61K 8/416* (2013.01); *A61Q 17/005* (2013.01); *D04H 1/4258* (2013.01); *A61K 2800/33* (2013.01)

(58) Field of Classification Search
CPC .... A61Q 17/005; A61K 8/416; A61K 8/0208; A01N 33/12
See application file for complete search history.

(56) References Cited

U.S. PATENT DOCUMENTS

| | | |
|---|---|---|
| 3,895,474 A | 7/1975 | Bauer |
| 4,408,996 A | 10/1983 | Baldwin |
| 4,666,621 A | 5/1987 | Clark et al. |
| 4,737,405 A | 4/1988 | Bouchette |
| 4,781,974 A | 11/1988 | Bouchette et al. |
| 4,847,088 A | 7/1989 | Blank |
| 4,941,989 A | 7/1990 | Kramer et al. |
| 4,946,617 A | 8/1990 | Sheridan et al. |
| 5,141,803 A | 8/1992 | Pregozen |
| 5,152,996 A | 10/1992 | Corey et al. |
| 5,419,908 A | 5/1995 | Richter et al. |
| 5,421,898 A | 6/1995 | Cavanagh |
| 6,214,363 B1 | 4/2001 | Beerse et al. |
| 6,258,368 B1 | 7/2001 | Beerse et al. |
| 6,258,455 B1 | 7/2001 | Clarke |
| 6,410,499 B1 | 6/2002 | Julemont et al. |
| 6,482,423 B1 | 11/2002 | Beerse et al. |
| 6,488,948 B1 | 12/2002 | Danicli |
| 6,610,314 B2 | 8/2003 | Koenig et al. |
| 6,667,290 B2 | 12/2003 | Svendsen |
| 6,838,078 B2 | 1/2005 | Wang et al. |
| 6,916,776 B2 | 7/2005 | Svendsen |
| 6,936,580 B2 | 8/2005 | Sherry et al. |
| 6,994,890 B2 | 2/2006 | Ohlhausen et al. |
| 7,160,846 B2 | 1/2007 | Biering et al. |
| RE40,495 E | 9/2008 | Svendsen |
| 7,432,234 B2 | 10/2008 | Ochomogo et al. |
| 7,485,589 B2 | 2/2009 | Ellis |
| 7,700,530 B2 | 4/2010 | Mundschau et al. |
| 7,799,751 B2 | 9/2010 | Kilkenny et al. |
| 7,858,106 B2 | 12/2010 | Nonaka |
| 7,998,495 B2 | 8/2011 | Argo et al. |
| 8,287,657 B2 | 10/2012 | Song et al. |
| 8,388,922 B2 | 3/2013 | Luu et al. |
| 8,486,427 B2 | 7/2013 | Colman et al. |
| 8,545,862 B2 | 10/2013 | Toreki et al. |
| 2002/0049257 A1 | 4/2002 | Natsch |
| 2002/0155969 A1 | 10/2002 | Rees et al. |
| 2002/0166573 A1* | 11/2002 | Policicchio ............... C11D 3/43 134/6 |

(Continued)

FOREIGN PATENT DOCUMENTS

| | | |
|---|---|---|
| EP | 1488815 | 12/2004 |
| EP | 1747258 | 1/2007 |
| WO | WO 2004/041312 | 5/2004 |

OTHER PUBLICATIONS

Tencel (http://naturescrusaders.com:80/wordpress/tencel®-or-lyocell-ecofriendly-caution-for-those-with-mcs) 2014, pp. 1-4 (Year: 2014).*

(Continued)

*Primary Examiner* — Andrew S Rosenthal
(74) *Attorney, Agent, or Firm* — Merchant & Gould P.C.

(57) ABSTRACT

An antimicrobial wipe is provided including a textile comprised of natural fibers untreated with a chemical bonding agent, the textile is treated with an antimicrobial composition, the antimicrobial composition comprising a quaternary ammonium compound and an organic acid, wherein the antimicrobial composition is surfactant free, emollient free, and polymeric free. A method of preparing such wipes is also provided.

12 Claims, 2 Drawing Sheets

(56) References Cited

U.S. PATENT DOCUMENTS

| | | |
|---|---|---|
| 2003/0143263 A1 | 7/2003 | Durden |
| 2003/0194932 A1 | 10/2003 | Clark et al. |
| 2004/0137815 A1 | 7/2004 | Ellis et al. |
| 2004/0228904 A1 | 11/2004 | Ellis et al. |
| 2005/0239356 A1 | 10/2005 | Parsons et al. |
| 2006/0128248 A1 | 6/2006 | Ellis |
| 2007/0142261 A1 | 6/2007 | Clark et al. |
| 2007/0237807 A1 | 10/2007 | Luu et al. |
| 2009/0285871 A1 | 11/2009 | Cunningham et al. |
| 2010/0113537 A1 | 5/2010 | Nonaka |
| 2010/0136074 A1 | 6/2010 | Bukshpan et al. |
| 2010/0207805 A1 | 8/2010 | Haworth |
| 2011/0177148 A1 | 7/2011 | Dicosimo et al. |
| 2012/0045496 A1 | 2/2012 | Short et al. |
| 2012/0070480 A1 | 3/2012 | Amos et al. |
| 2012/0070481 A1 | 3/2012 | Bolkan et al. |
| 2012/0171155 A1 | 7/2012 | Cunningham et al. |
| 2012/0171300 A1 | 7/2012 | Koenig et al. |
| 2012/0207805 A1 | 7/2012 | Colman et al. |
| 2013/0058880 A1 | 3/2013 | Dong |

OTHER PUBLICATIONS

SolvSat (https://www.texwipe.com/products/wipers-all/by-wiper-type/pre-wet-wipers/industrial-wipers/solvent-cleaners/acetone.aspx) 2011, p. 1 (Year: 2011).*

Getman, Gerry, *An Advanced Polymeric Antimicrobial for Non Woven Fabrics and Solid Materials including Spun Plastic Resins*, Sep. 2007, Presentation from INDA/TAPPI International Nonwovens Technical Conference.

Bourgeois, *Fibres with Antiseptic Action*, Index 93 Congress, Session. 3D: R&D—Polymer fibres & surface modification at Institut Textile de France, 1993.

Masuku, S. M., et al. "Cleaning and decontamination efficacy of wiping cloths and sliver dihydrogen citrate on food contact surfaces," *Journal of Applied Microbiology* vol. 113, pp. 89-95, ISSN 1364-5072, 2012.

Lonza (http://www.fankim.com/media/Lonza_MSDSMaterialSafetyDataSheets_Bardac_205-M.pdf), Dec. 10, 2010, pp. 1-14.

AkzoNobel "Cationic and Quaternary Surfactants" (http://sc.akzonobel.com/en/agriculture/Documents/A4_size/AkzoNobel_tb_81_Agro_Cationic_and_Quaternary_Surfactants_A4.pdf) Aug. 2009, pp. 1-8.

* cited by examiner

DISPOSABLE ANTIMICROBIAL WIPES AND METHODS OF MAKING

CROSS REFERENCE TO RELATED APPLICATION

The present application is a continuation of Ser. No. 14/682,663, filed Apr. 9, 2015, the disclosure of which is hereby incorporated in its entirety.

FIELD

The invention generally relates to articles for cleaning and/or sanitizing a surface. More particularly, the invention relates to the combination of substrates and chemistries particularly suitable for delivering a disinfectant or antimicrobial agent. The invention also relates to substrates treated with such a disinfectant or antimicrobial agent and methods of preparing such disposable wipes

BACKGROUND

Disposable substrates are commonly used in cleaning applications. Suitable substrates include woven and nonwoven fabrics and various combinations thereof. Such substrates have been saturated with cleaning agents such as disinfectants, solvents, anti-microbials, detergents and the like. The resulting cleaning products fabricated from such saturated substrates are accepted as a convenient and practical means for cleaning surfaces.

Nonwoven surface cleaning or sanitizing articles fabricated for the food service or hospitality industry often include a blend of synthetic or natural fiber, as well as a binder formulation. Such sanitizing articles are more popular as compared to terry cloth towels due to the benefits derived from using a limited or single use sanitizing or cleaning article. Reusable damp woven terry cloth towels are thought to be more susceptible to bacterial build up as they are left standing wet between uses.

As the use of disposable sanitizing wipes has increased, nonwoven fabrics have been engineered to facilitate the sanitizing process of food preparation and serving surfaces. Despite these developments, it has been found that certain nonwoven fabrics have a detrimental effect on a sanitizing solution. It has been found that the inherent or applied ionic properties of the sanitizing and/or cleaning article may neutralize the effectiveness of the sanitizing solution over time. Many wipe or towel substrates possess good absorption of antimicrobial solutions but many bind via chemical affinity interactions with acid-anionic antimicrobials such as quaternary ammonium antimicrobials. This second property known as adsorption does not allow recovery or expression of the antimicrobial agents of use-solutions. Such adsorption results in failure to produce the desired anti-microbial efficacy. When attempting to deliver an antimicrobial agent this is an unwelcome property and is not easily overcome.

It is desirable to use natural fibers for the disinfectant wipes, however, such natural fibers often tenaciously bind the disinfectant chemicals thereby prohibiting expression onto a surface. A need exists for a disposable wipe that is inexpensive and does not require additional coatings or binders in order to allow the disinfectant to release from the substrate. There is also a need for a disposable external surface cleaning and/or sanitizing wipe that may be used in conjunction with quaternary ammonium disinfectant or antimicrobial which does not interact with or impede the delivery of the disinfectant to the intended surface.

The art is replete with coatings useful for overcoming the binding affinity by the substrate for the disinfectant. They generally focus upon aiding the release or expression of quaternary actives. However, such coatings add another step, additional chemicals, and added expense to a single use disinfectant wipe. To date the industry has attempted to eliminate or mitigate interaction between the disinfectant and the substrate by pretreating the substrate with the disinfectant. Such a pretreatment in essence saturates the substrate. A method of reducing the interaction between the disinfectant and the substrate involves coating the substrate with a chemical to neutralize the substrate such that the substrate no longer binds or interacts with the disinfectant.

A need exists for a disposable wipe that is inexpensive and does not require additional coatings in order to allow the disinfectant to release from the substrate. There is also a need for a disposable external surface cleaning and/or sanitizing wipe that may be used in conjunction with an antimicrobial agent which does not interact with or impede the delivery of the disinfectant to the intended surface. The present invention provides an elegant solution to reduce or eliminate the interaction of substrate with disinfectant.

SUMMARY

The present invention provides a disposable antimicrobial wipe useful to sanitize surfaces. The surfaces for sanitizing are primarily hard surfaces. The antimicrobial wipes of the invention provide quick release of the antimicrobial agent or antimicrobial chemistry. The antimicrobial wipe of the invention includes a textile comprised of natural fibers that is not treated with a chemical binding agent but is treated with an antimicrobial composition. The antimicrobial treatment composition includes a quaternary ammonium compound and an organic acid, wherein the antimicrobial composition is surfactant free, emollient free and polymeric free. While those skilled in the art will recognize that quaternary ammonium compounds may be categorized as cationic surfactants, the invention anticipates that no surfactants are added to the antimicrobial chemistry composition added to the disposable wipes beyond or in addition to the quaternary ammonium compound(s).

In an embodiment the textile used in the antimicrobial wipe is formulated from a woven or nonwoven web. Fibers useful for making the textile used in the antimicrobial wipe of the invention include cotton, cellulose, wood pulp, wool, silk, ramie, rayon, flax, hemp, sisal, jute, kenaf, bamboo, coconut, TENCEL®, LYOCELL, or combinations thereof. The textile used to prepare the antimicrobial wipe of the invention may further include synthetic fibers.

The organic acid useful for treating textiles to prepare wipes of the invention include citric acid, maleic acid, tartaric acid, salicylic acid, glycolic acid, adipic acid, glutaric acid, gluconic acid, succinic acid, benzoic acid, lactic acid, acetic acid, malic acid, or combinations thereof. In an embodiment of the invention the organic acid has a pKa from about 2 to about 7. In an embodiment of the invention textiles used to prepare antimicrobial wipes of the invention are treated with about 0.05 wt. % to about 0.4 wt. % quaternary ammonium and about 0.05 wt. % to about 0.4 wt. % organic acid.

Antimicrobial wipes of the invention provide release or expression of greater than 40% of the quaternary ammonium when squeezing the wipe for about 2 to about 30 seconds, or about 5 to about 20 seconds. In another embodiment the antimicrobial wipe of the invention releases greater than 50% of the quaternary ammonium after squeezing the wipe for about 5 to about 20 seconds.

Quaternary ammonium compounds useful for preparing antimicrobial wipes of the invention include octyl decyl dimethyl ammonium chloride, dioctyl dimethyl ammonium chloride, didecyl dimethyl ammonium chloride, dimethyl ethyl benzyl ammonium chloride, didecyl dimethyl ammonium carbonate, didecyl dimethyl ammonium bicarbonate, benzethonium chloride, and combinations thereof. Antimicrobial wipes of the invention may further be treated with dye, fragrance, alcohol or any combination thereof.

A method of preparing a disposable antimicrobial wipe is also disclosed. The method involves applying organic acid and quaternary ammonium to a natural fiber textile. In an embodiment the organic acid and quaternary ammonium are added to the textile simultaneously. In another embodiment the organic acid and quaternary ammonium are added consecutively to the textile. It is expected that better expression of the quaternary ammonium compound occurs if (1) the organic acid is added before the quaternary ammonium or (2) the organic acid is added simultaneously with the quaternary ammonium, rather than if the (3) quaternary ammonium is added before the organic acid. Without being bound by theory it is believed that the quaternary ammonium would saturate the textile not allowing the later added organic acid to access the textile. In an embodiment a vendor may offer disposable textile wipes that have been contacted with an organic acid for sale to customers along with a separate quaternary ammonium compound to be added to the wipe container by the customer before use. The textile may be dried after contact with the organic acid and before sale to the customer with the separate quaternary ammonium compound.

In the method of preparing antimicrobial wipes organic acids such as citric acid, maleic acid, tartaric acid, salicylic acid, glycolic acid, adipic acid, glutaric acid, succinic acid, benzoic acid, lactic acid, acetic acid, malic acid, or combinations thereof may be used. In methods of the invention the organic acid used to treat the textile has a pKa from about 2 to about 7. In an embodiment the organic acid has a pKa of about 2 to about 6.

In methods of preparing antimicrobial wipes of the invention about 0.05 wt. % to about 0.4 wt. % quaternary ammonium and about 0.05 wt. % to about 0.4 wt. % organic acid is applied to the textile. The weight percent of the quaternary ammonium and organic acid is based on the use solution. That is, 0.05% weight percent is the same as 500 ppm and 0.4% is equivalent to 4000 ppm. Regulations require that food safe contact surfaces include a minimum of 150 ppm quaternary ammonium whereas healthcare surfaces require 4000 ppm quaternary ammonium based on actives. Greater than 40% of the quaternary ammonium is expressed after squeezing the wipe for 5-20 seconds prepared according to the invention method. In another embodiment greater than 50% of the quaternary ammonium is expressed after squeezing the wipe for 5-20 seconds.

A pretreated antimicrobial wipe is also disclosed. Such pretreated wipe consists of a textile of natural fibers treated with pretreatment chemistry consisting of an organic acid and water. The pretreated wipe may further consist of quaternary ammonium and water combination added to the pretreated wipe. Such pretreatment chemistry used to prepare a pretreated antimicrobial wipe of the invention may consist of surfactant, dye, fragrance, alcohol or any combination thereof.

Antimicrobial wipes prepared according to the method of the invention may include disposable textiles wherein the textile consists of a woven or nonwoven web. Natural fibers are used to prepare the disposable textile used in the method of preparing antimicrobial wipes. Such natural fibers consist of cotton, cellulose, wood pulp, wool, silk, ramie, rayon, flax, hemp, sisal, jute, kenaf, bamboo, coconut, TENCEL®, LYOCELL, or combinations thereof.

A method of preparing an antimicrobial wipe is provided. The method includes a first step of applying organic acid to a textile comprised of natural fibers, and a second step of applying quaternary ammonium to the textile.

DETAILS OF THE INVENTION

Figure 1:
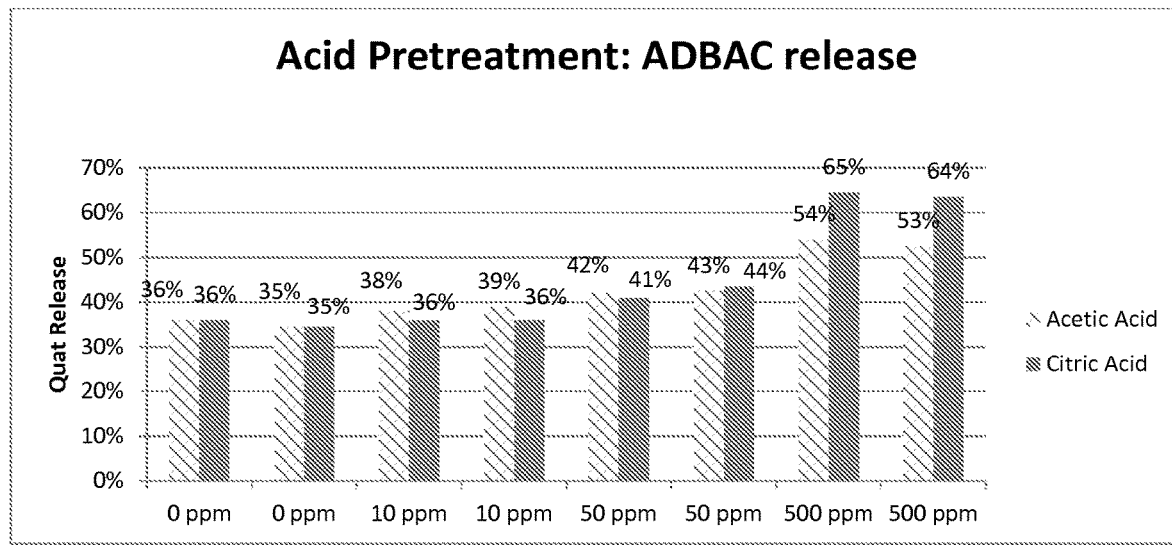
FIG. 1 is a graph illustrating the release of dimethyl benzyl ammonium chloride comparing using citric acid as the organic acid comparing the release of dimethyl benzyl ammonium chloride using glacial acetic acid as the organic acid.

"Cleaning" means to perform or aid in soil removal, bleaching, microbial population reduction, rinsing, or combination thereof.

As used herein, weight percent (wt %), percent by weight, % by weight, and the like are synonyms that refer to the concentration of a substance as the weight of that substance divided by the total weight of the composition and multiplied by 100.

As used herein, the term "about" modifying the quantity of an ingredient in the compositions of the invention or employed in the methods of the invention refers to variation in the numerical quantity that can occur, for example, through typical measuring and liquid handling procedures used for making use solutions in the real world; through inadvertent error in these procedures; through differences in the manufacture, source, or purity of the ingredients employed to make the compositions or carry out the methods; and the like. The term about also encompasses amounts that differ due to different equilibrium conditions for a composition resulting from a particular initial mixture. Whether or not modified by the term "about," the claims include equivalents to the quantities.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

In the interest of brevity and conciseness, any ranges of values set forth in this specification contemplate all values within the range and are to be construed as support for claims reciting any sub-ranges having endpoints which are real number values within the specified range in question. By way of a hypothetical illustrative example, a disclosure in this specification of a range of from 1 to 5 shall be considered to support claims to any of the following ranges: 1-5; 1-4; 1-3; 1-2; 2-5; 2-4; 2-3; 3-5; 3-4; and 4-5.

The term "substantially free" may refer to any component that the composition of the invention lacks or mostly lacks. When referring to "substantially free" it is intended that the component is not intentionally added to compositions of the invention. Use of the term "substantially free" of a component allows for trace amounts of that component to be included in compositions of the invention because they are present in another component. However, it is recognized that only trace or de minimus amounts of a component will be allowed when the composition is said to be "substantially free" of that component. Moreover, the term if a composition is said to be "substantially free" of a component, if the component is present in trace or de minimus amounts it is understood that it will not affect the effectiveness of the composition. It is understood that if an ingredient is not expressly included herein or its possible inclusion is not stated herein, the invention composition may be substantially free of that ingredient. Likewise, the express inclusion of an ingredient allows for its express exclusion thereby allowing a composition to be substantially free of that expressly stated ingredient.

As used herein the term, "consisting essentially of" in reference to a composition refers to the listed ingredients and does not include additional ingredients that, if present, would affect the cleaning ability of the cleaning composition. The term "consisting essentially of" may also refer to a component of the cleaning composition. For instance, a surfactant package may consist essentially of two or more surfactants and such surfactant package would not include any other ingredients that would affect the effectiveness of that surfactant package—either positively or negatively. As used herein the term "consisting essentially of" in reference to a method of cleaning or preparing a disinfecting wipe refers to the listed steps and does not include additional steps (or ingredients if a composition is included in the method) that, if present, would affect the cleaning ability of the cleaning method or the efficacy of the antimicrobial wipe.

As used herein, the term "microorganism" refers to any noncellular or unicellular (including colonial) organism. Microorganisms include all prokaryotes. Microorganisms include bacteria (including cyanobacteria), spores, lichens, fungi, protozoa, virinos, viroids, viruses, phages, and some algae. As used herein, the term "microbe" is synonymous with microorganism.

As used herein, the term "sanitizer" refers to an agent that reduces the number of bacterial contaminants to safe levels as judged by public health requirements. In an embodiment, sanitizers for use in this invention will provide at least a 99.999% reduction (5-log order reduction). These reductions can be evaluated using a procedure set out in Germicidal and Detergent Sanitizing Action of Disinfectants, Official Methods of Analysis of the Association of Official Analytical Chemists, paragraph 960.09 and applicable sections, 15th Edition, 1990 (EPA Guideline 91-2). The EPA Methods and Guidelines are hereby incorporated by reference in their entirety for all purposes. According to this reference a sanitizer should provide a 99.999% reduction (5-log order reduction) within 30 seconds at room temperature, 25±2° C., against several test organisms.

As used herein, the term "disinfectant" refers to an agent that kills all vegetative cells including most recognized pathogenic microorganisms, using the procedure described in A.O.A.C. Use Dilution Methods, Official Methods of Analysis of the Association of Official Analytical Chemists, paragraph 955.14 and applicable sections, 15th Edition, 1990 (EPA Guideline 91-2). Such EPA Procedures and Guidelines are hereby incorporated by reference in their entirety for all purposes. As used herein, the term "high level disinfection" or "high level disinfectant" refers to a compound or composition that kills substantially all organisms, except high levels of bacterial spores, and is effected with a chemical germicide cleared for marketing as a sterilant by the Food and Drug Administration. As used herein, the term "intermediate-level disinfection" or "intermediate level disinfectant" refers to a compound or composition that kills Mycobacteria, most viruses, and bacteria with a chemical germicide registered as a tuberculocide by the Environmental Protection Agency (EPA). As used herein, the term "low-level disinfection" or "low level disinfectant" refers to a compound or composition that kills some viruses and bacteria with a chemical germicide registered as a hospital disinfectant by the EPA.

Differentiation of antimicrobial "-cidal" or "-static" activity, the definitions which describe the degree of efficacy, and the official laboratory protocols for measuring this efficacy are considerations for understanding the relevance of antimicrobial agents and compositions. Antimicrobial compositions can affect two kinds of microbial cell damage. The first is a lethal, irreversible action resulting in complete microbial cell destruction or incapacitation. The second type of cell damage is reversible, such that if the organism is rendered free of the agent, it can again multiply. The former is termed microbiocidal and the later, microbiostatic. A sanitizer and a disinfectant are, by definition, agents which provide antimicrobial or microbiocidal activity. In contrast, a preservative is generally described as an inhibitor or microbiostatic composition.

The term "disposable" as used herein refers to a substrate or textile that is discarded after one use.

As used herein, the term "chemical binding agent" or "chemical bind-diminishing agent" or "coating" refers to chemical treatments applied to the substrate before application of the microbial agent which are normally used to ensure expression of disinfectant chemicals from disposable wipes. Examples of such coating agents include polymeric coatings as provided in U.S. Pat. No. 6,258,368; US 2010/0207805; U.S. Pat. No. 5,152,996; US 2012/0045496; and U.S. Pat. No. 8,486,427.

The present invention contemplates the possibility of omitting any components listed herein. The present invention further contemplates the omission of any components even though they are not expressly named as included or excluded from the invention.

These and other aspects, advantages, and salient features of the present invention will become apparent from the following description and the appended claims.

The present invention begins with a suitable substrate. A suitable substrate of the invention does not allow the disinfectant or antimicrobial chemistry to adsorb to the textile. In accordance with the present invention, the substrate includes natural fiber. Suitable natural fibers useful to prepare textiles for use as the disposable wipes used to carry antimicrobials of the invention include cotton, cellulose, wood pulp, wool, silk, ramie, rayon, flax, hemp, linen, sisal, jute, kenaf, bamboo, coconut, TENCEL®, LYOCELL, or combinations thereof.

Lyocell is the generic name for a biodegradable made from treated wood pulp. Lyocell is commonly sold under the brand name Tencel®, manufactured by Lenzing AG based in Austria. Lyocell fabric is considered a natural rather than synthetic product because it is manufactured using plant material. The production process for lyocell begins by treating wood chips approximately the size of a coin until they form a substance similar to a thick paper, which is then sent to a fabric production factory. Once there, it is broken down into about 1 inch (about 2.5 cm) squares and chemically dissolved. The resulting slurry is then forced through a device called a spinneret, which has many small holes in it, somewhat like a strainer. This causes the mixture to form long fibers, which are chemically treated again, rinsed and dried, and lubricated before being compressed, combed, and cut. After this, they can be spun into yarn for use, either alone or in combination with other materials.

Textiles useful to prepare wipes of the present invention may further include synthetic fiber. Synthetic fibers that may be used in accordance with the present invention include those formed from polymers chosen from the group of thermoplastic polymers consisting of polyolefin, and polyesters wherein the polyolefins are chosen from the group consisting of polypropylene, polyethylene, polyamides and combinations thereof.

Textiles used to prepare antimicrobial wipes of the invention may be formulated from a woven or nonwoven web. Any method of preparing nonwoven webs may be used to prepare textiles useful in the present invention. Such methods include but are not limited to air laid or dry laid, carded, hydroentangled, melt blown, needlepunched, spunbond, spunlaced, and wetlaid. Fibers useful for making the textile used in the antimicrobial wipe of the invention include cotton, cellulose, wood pulp, wool, silk, ramie, rayon, flax, hemp, sisal, jute, kenaf, bamboo, coconut, TENCEL®, LYOCELL, or combinations thereof.

Basis weight is a common term in the nonwoven textile industry. The term is used to express how much a nonwoven fabric weighs per unit area. The term is derived from the papermaking industry. In most areas of the world basis weight is expressed as grams per square meter. In the United States, lightweight nonwovens such as diaper cover stock are generally provided in grams per square meter although the metric and English systems are sometimes mixed to express basis weight as grams per square yard. In heavier fabrics such as needlepunch, the basis weight is often given in ounces per square yard. The textile weight chosen for preparing disposable wipes of the invention will depend upon the intended use or intended market of the wipe. For example, a lighter weight textile may be more useful for medical as compared to food service surface disinfecting or the reverse may be true. The skilled practitioner is able to select the appropriate textile weight for the intended use.

The invention provides treating the textile with an organic acid either as a pretreatment or in combination with the antimicrobial agent. It has surprisingly been found that incorporating an organic acid either as a pretreatment of the textile or in combination with the antimicrobial chemistry allows the disinfectant or antimicrobial agent to release satisfactorily. In other words, by employing an organic acid in accordance with the present invention the antimicrobial agent does not adsorb to the surface of the textile allowing release or expression of the antimicrobial chemicals. Examples of suitable organic acids useful in preparing wipes of the invention include but are not limited to citric acid, maleic acid, tartaric acid, salicylic acid, glycolic acid, adipic acid, glutaric acid, gluconic acid, succinic acid, benzoic acid, lactic acid, acetic acid, malic acid, or combinations thereof. In an embodiment of the invention the organic acid has a pKa from about 2 to about 7. In another embodiment the organic acid has a pKa of about 2 to about 6, about 2 to about 5, about 2 to about 4, and about 2 to about 3. In another embodiment of the invention the organic acid has a pKa of about 2 to about 6, about 3 to about 6, about 4 to about 6, and about 5 to about 6. In another embodiment of the invention the organic acid has a pKa of about 3 to about 7, about 4 to about 7, about 5 to about 7, and about 6 to about 7. In yet another embodiment of the invention the organic acid has a pKa of about 3 to about 4, 3 to about 5, and about 4 to about 5.

Antimicrobial agents useful in preparing disposable disinfectant wipes according to the invention include quaternary ammonium compounds. Exemplary quaternary ammonium compounds having antimicrobial properties include but are not limited to alkyl dimethyl benzyl ammonium chloride having an alkyl chain length of 8-18 carbon atoms. Such compositions are commonly referred to a benzalkonium chloride compositions. Further examples of quaternary ammonium compounds include but are not limited to octyl decyl dimethyl ammonium chloride, dioctyl dimethyl ammonium chloride, didecyl dimethyl ammonium chloride, dimethyl ethyl benzyl ammonium chloride, didecyl dimethyl ammonium carbonate, didecyl dimethyl ammonium bicarbonate, benzethonium chloride, myristyl trimethyl ammonium chloride, methyl benzethonium chloride, cetalkonium chloride, cetrimonium bromide (CTAB), carnitine, dofanium chloride, tetraethyl ammonium bromide (TEAB), domiphen bromide, benzododecinium bromide, benzoxonium chloride, choline, cocamidopropyl betaine (CAPB), denatonium, dimethyl dioctyadecyl ammonium chloride, and combinations thereof. When preparing chemistry for addition to textiles in order to practice the invention, a single quaternary ammonium compound may be used in combination with an organic acid or a plurality of quaternary ammonium compounds may be combined.

While those skilled in the art will recognize that quaternary ammonium compounds may be categorized as cationic surfactants, the invention anticipates that no surfactants are added to the antimicrobial chemistry composition beyond or in addition to the quaternary ammonium compound(s). That is, the antimicrobial chemistry applied to the textiles to comprise the disposable wipes of the invention are surfactant free apart from the quaternary ammonium compound(s).

The invention particularly envisions excluding from use silane quaternary ammonium compounds. Moreover, emollients and polymeric binding agents may be omitted from antimicrobial wipes of the invention.

In particular, the present invention provides a disposable disinfectant wipe using a quaternary ammonium as a component in the antimicrobial or disinfecting chemistry that is readily expressed from the textile. The invention accomplishes the expression of a quaternary ammonium without use of and without requiring a chemical bind-diminishing agent or coating which are normally used to ensure expression of disinfectant chemicals from disposable wipes.

Disposable disinfectant wipes of the invention or prepared according to the method of the invention are useful for cleaning hard surfaces. Examples of such hard surfaces include but are not limited to glass, tile, ceramic, stainless steel, aluminum, plastic, marble, granite, metal, and the like. Antimicrobial wipes of the invention may be useful in preparing or cleaning food service or kitchen surfaces or counters, medical or examination tables or counters, appliance surfaces, door handles, and the like. One skilled in the art will recognize the usefulness of the present invention for sanitizing or disinfecting surfaces and will further appreciate the benefit to throwing away such wipe after one use.

The disinfectant or antimicrobial chemistry applied onto the substrate or textile may optionally further include one or more additives such as fragrances, dyes, pigments, emollients, bleaching agents, anti-static agents, anti-wrinkling agents, odor removal/odor capturing agents, ultraviolet light protection agents, insect repellency agents, souring agents, mildew removing agents, allergicide agents, and mixtures thereof. However, none of these optional additives are intended to serve as a bond-diminishing coating on the substrate. It is envisioned that such optional/additional ingredients would be added with the disinfectant to the substrate or textile surface. If such optional/additional ingredients act to allow the disinfectant to release from the substrate, such optional/additional ingredients would not be used to pretreat the substrate. That is, the optional or additional ingredients would not be added to the substrate before the disinfectant.

Disinfectant or antimicrobial chemistries are coated onto the substrate for length of times from about 20 seconds, 30 seconds, 45 seconds, 1 minute, 2 minutes, 5 minutes, 10 minutes and up to about days, months, and even years. Pre-coated wipes may be sold in airtight containers. Such pre-coated wipes may be in contact with the disinfectant for days, months and up to and including years. The present invention allows release of the quaternary ammonium-containing disinfectant from the wipes no matter the length of the application or soaking time.

Disposable wipes of the invention are prepared by either applying the organic acid to the textile first or by applying the organic acid to the wipe textile in the presence of the quaternary ammonium compound. In the first option the textile is pretreated with organic acid. In an embodiment about 5 grams to about 80 grams of about 100 ppm to about 1000 ppm organic acid solution is added to about 1 to about 5 g textiles. In another embodiment about 10 grams to about 50 grams of about 200 ppm to about 800 ppm organic acid solution is added to about 1.5 to about 4.5 g textiles. In another embodiment about 15 grams to about 45 grams of about 300 ppm to about 700 ppm organic acid solution is added to about 2 to about 4.0 g textiles. In another embodiment about 17.5 grams to about 40 grams of about 400 ppm to about 600 ppm organic acid solution is added to about 2.1 to about 3.5 g textiles. In another embodiment about 20 grams to about 35 grams of about 300 ppm to 900 ppm organic acid solution is added to about 1 to about 5 g textiles. In another embodiment about 25 grams to about 35 grams of about 400 ppm to 800 ppm organic acid solution is added to about 1 to about 5 g textiles. In another embodiment about 25 grams to about 35 grams of about 400 ppm to 800 ppm organic acid solution is added to about 1 to about 5 g textiles. In another embodiment about 25 grams to about 35 grams of about 350 ppm to 650 ppm organic acid solution is added to about 1 to about 5 g textiles.

If the organic acid precedes addition of the quaternary ammonium compound the wipe may be dried overnight or for some shorter time to allow for the textile to become substantially dry. One having ordinary skill in the art will appreciate that the term "dry" is relative to the humidity in the ambient air. If the relative humidity is low a cotton fiber textile is said to be bone dry when the moisture content is within about 7 to about 9 weight percent. The present invention does not require that the moisture content of the textile be "bone dry" before applying the antimicrobial agent. Rather, the textile may have a moisture content up to about 15 weight percent and still feel dry to the touch. Once the textile is dry or substantially dry it is soaked or immersed in 1000 ppm quaternary ammonium for from about 20 seconds up to about 24 hours to about 2 days up to 2 years. If the organic acid precedes addition of the quaternary ammonium compound the wipe may be immediately soaked or immersed in 1000 ppm quaternary ammonium for from about 20 seconds up to about 24 hours to about 2 days.

In an embodiment from about 300 ppm to about 2000 ppm quaternary ammonium is used to soak the textile, about 350 ppm to about 1900 ppm quaternary ammonium, about 400 ppm to about 1800 ppm quaternary ammonium, about 500 ppm to about 1700 ppm quaternary ammonium, about 600 ppm to about 1600 ppm quaternary ammonium, about 700 ppm to about 1500 ppm quaternary ammonium, about 800 ppm to about 1400 ppm quaternary ammonium, about 900 ppm to about 1200 ppm quaternary ammonium, and about 950 ppm to about 1100 ppm quaternary ammonium.

In the second option organic acid is added directly onto the textiles in the presence of quaternary ammonium so that the quaternary ammonium level is about 1000 ppm and the organic acid level is about 500 ppm. About 30 grams of 1000 ppm of the organic acid/quaternary ammonium solution is added to the about 1.5 to about 3.5 grams of textiles and the textiles are allowed to soak in the solution for about 24 hours.

The following non-limiting Examples are provided as illustrative embodiments of the invention. Notwithstanding that the numerical ranges and parameters setting forth the broad scope of the invention are approximations, the numerical values set forth in the specific examples are reported as precisely as possible. Any numerical values, however, inherently contain certain errors necessarily resulting from the standard deviation found in their respective testing measurements.

Example 1

Wipes were prepared using Tencel® textiles. Chemical compositions provided in the table below were applied to three different sets of wipes. The chemicals were added to the textile simultaneously. That is, whenever an organic acid and quaternary ammonium were applied to the wipes they were applied together (Test 1 and Test 2). The resultant wipes were tested for expression of the antimicrobial quaternary ammonium compound by using the squeeze method. The squeeze method was accomplished by squeezing a single ply 3"×3" textile by hand for about 5 to about 20 seconds until all free liquid was dispensed and until the textile was no longer dripping liquid. The amount of expressed liquid was collected and the amount of quaternary ammonium was tested using high pressure liquid chromatography (HPLC).

TABLE 1

| Raw Material (% active) | Control | Test 1 | Test 2 |
|---|---|---|---|
| Bardac* 205M (50%) | 33.3% | 33.3% | 33.3% |
| Citric acid monohydrate (100%) | 0 | 16.7% | 0 |
| Glacial Acetic acid (100%) | 0 | 0 | 16.7% |
| Water | 66.7% | 50% | 50% |
| SX 928** | Substrate | Substrate | Substrate |

*Bardac 205M is available from Lonza and is a blend of twin chain quaternary ammonium compounds and alkyl dimethyl benzyl ammonium chloride (ADBAC)
**SX928 is a 100% TENCEL ® nonwoven textile manufactured without chemical binder available from Suominen (based in Poland) having a basis weight of 50 g/m², thickness of 0.75 mm, absorbent capacity of 11.5 g/g and an absorbent rate of 1.2 seconds.

The release of dimethyl benzyl ammonium chloride comparing Test 1 (citric acid as the organic acid) vs. Test 2 (glacial acetic acid as the organic acid) is shown FIG. 1. The 0ppm noted in FIG. 1 is the control which provides the amount of quaternary ammonium alone expressed because 0ppm organic acid was added to the samples. The results show that as the concentration of the organic acid increased, the greater the expression of the quaternary ammonium compound.

Example 2

Wipes were prepared as described in Example 1 above. Glacial acetic acid and citric acid at concentrations of 10 ppm, 50 ppm, and 500 ppm were separately applied to the Tencel® substrates along with Bardac 205 quaternary ammonium. The wipes were prepared in duplicate. The organic acid and quaternary ammonium chemicals were added to the textile simultaneously. The chemistry was allowed to soak the textiles for 24 hours. The resultant wipes were tested for expression of the antimicrobial quaternary ammonium compound by using the squeeze method. The squeeze method as explained above was accomplished, the amount of expressed liquid was collected and the amount of quaternary ammonium was tested using HPLC.

Figure 2:
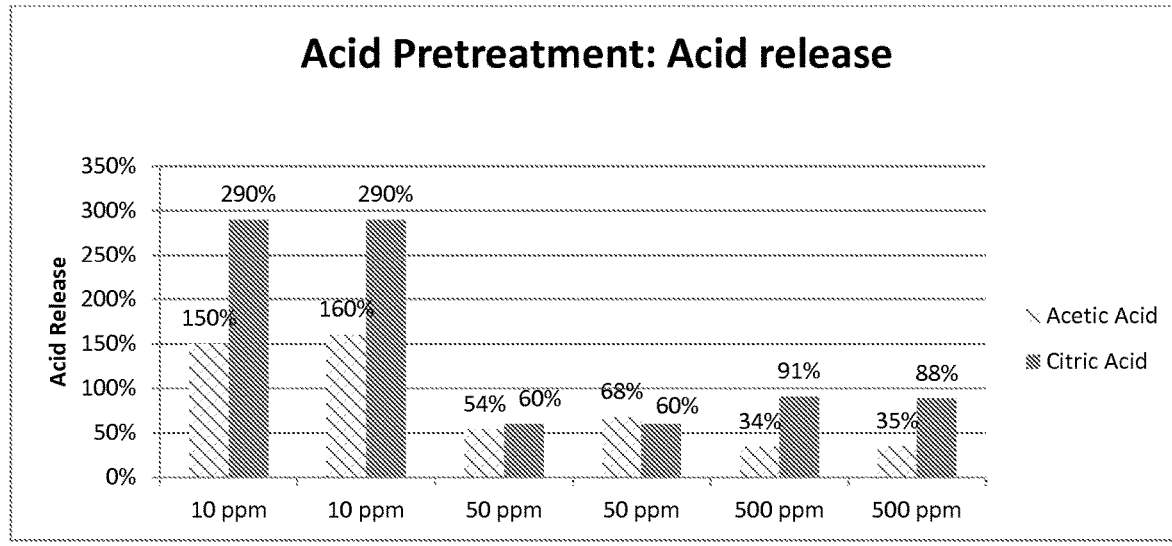
FIG. 2 is a graph illustrating the release of acid comparing different concentrations of citric acid and different concentrations of glacial acetic acid.
Figure 3:
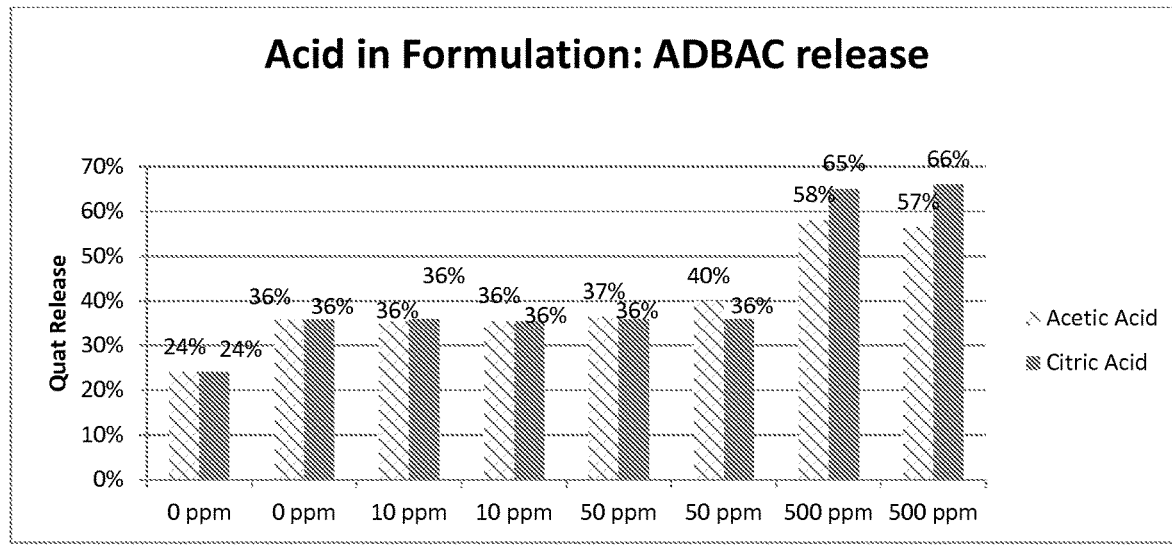
FIG. 3 is a graph illustrating the release of dimethyl benzyl ammonium chloride comparing different concentrations of citric acid and different concentrations of glacial acetic acid.

The release of acid comparing the different concentrations of citric acid and the different concentrations of glacial acetic acid is shown FIG. 2. Note that the acid analysis for 10 ppm acid treatment is over 100% and is erroneous due to the limit of detection for HPLC. The release of dimethyl benzyl ammonium chloride comparing the different concentrations of citric acid and the different concentrations of glacial acetic acid is provided in FIG. 3. Again, note that the acid analysis for 10 ppm acid treatment is over 100% and is erroneous since HPLC cannot detect such low limits.

Example 3

Wipes were prepared as described in Example 1 above. Citric acid at concentrations of 0ppm, 500 ppm, 1000 ppm, 2000 and 4000 ppm were separately applied to the Tencel® substrates along with Bardac 205 quaternary ammonium. The wipes were prepared in duplicate. The organic acid and quaternary ammonium chemicals were added to the textile simultaneously. The following is a table showing the pH of citric acid and acetic acid at varying concentrations:

| Concentration | pH of Citric Acid | pH of Acetic Acid |
|---|---|---|
| 10 ppm | 2.48 | 2.69 |
| 50 ppm | 2.58 | 2.62 |
| 500 ppm | 2.65 | 2.56 |

The chemistry was allowed to soak the textiles for 24 hours. The resultant wipes were tested for expression of the antimicrobial quaternary ammonium compound by using the squeeze method. The squeeze method as described above was employed to express liquid from the textiles. The expressed liquid was collected and the amount of quaternary ammonium was tested using HPLC.

Figure 4:
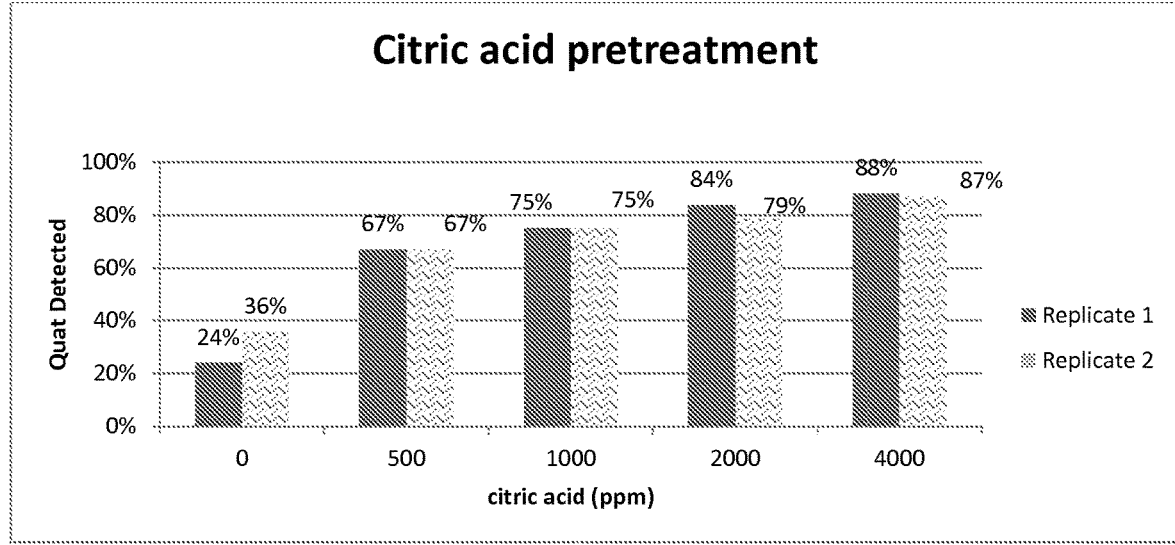
FIG. 4 is a graph illustrating the release of dimethyl benzyl ammonium chloride with different concentrations of citric acid.

The release of dimethyl benzyl ammonium chloride comparing the different concentrations of citric acid is shown FIG. 4. As the citric acid concentration increased, the amount of quaternary ammonium released also increased.

While typical aspects of embodiment and/or embodiments have been set forth for the purpose of illustration, the foregoing description and the accompanying drawings should not be deemed to be a limitation on the scope of the invention. Accordingly, various modifications, adaptations, and alternatives may occur to one skilled in the art without departing from the spirit and scope of the present invention. It should be understood that all such modifications and improvements have been deleted herein for the sake of conciseness and readability but are properly within the scope of the following claims.

We claim:

1. A method of preparing an antimicrobial wipe comprising:
   (a) applying a first composition to a textile comprising rayon fibers, wherein the first composition comprises water and from about 0.05 to about 0.4 wt. % of an organic acid and is substantially free of quaternary ammonium, and wherein the fibers are not treated with a polymeric coating binding agent; and thereafter
   (b) applying a second composition to the textile, wherein the second composition comprises a quaternary ammonium compound;
   wherein at least 40% of the quaternary ammonium compound is released from the wipe when the wipe is squeezed by hand until no more liquid is released from the wipe.

2. The method of claim 1, wherein the applying the first composition to a textile comprises applying about 5 grams to about 80 grams of the first composition to about 1 gram to about 5 grams of the textile.

3. The method of claim 1 further comprising drying the textile after applying the first composition to allow for the textile to become substantially dry before applying the second composition.

4. The method of claim 1, wherein the second composition comprises about 0.05% to about 0.4 wt. % of quaternary ammonium.

5. The method of claim 1, wherein the second composition comprises at least about 0.1 wt. % of quaternary ammonium.

6. The method of claim 1, wherein the wipe is disposable.

7. The method of claim 1, wherein the organic acid is selected from the group consisting of citric acid, maleic acid, tartaric acid, salicylic acid, glycolic acid, adipic acid, glutaric acid, gluconic acid, succinic acid, benzoic acid, lactic acid, acetic acid, malic acid, and combinations thereof.

8. The method of claim 1, wherein the organic acid has a pKa from 2 to 7.

9. The method of claim 1 wherein the organic acid has a pKa of 2 to 6.

10. The method of claim 1, wherein greater than 40% of the quaternary ammonium is expressed after squeezing the wipe for 5-20 seconds.

11. The method of claim 1, wherein greater than 50% of the quaternary ammonium is expressed after squeezing the wipe for 5-20 seconds.

12. The method of claim 1, wherein the quaternary ammonium is selected from the group consisting of octyl decyl dimethyl ammonium chloride, dioctyl dimethyl ammonium chloride, didecyl dimethyl ammonium chloride, dimethyl ethyl benzyl ammonium chloride, didecyl dimethyl ammonium carbonate, didecyl dimethyl ammonium bicarbonate, benzethonium chloride, and combinations thereof.

* * * * *